United States Patent
Engelhardt et al.

(10) Patent No.: US 8,589,106 B2
(45) Date of Patent: Nov. 19, 2013

(54) CALIBRATION OF A HANDHELD DIABETES MANAGING DEVICE THAT RECEIVES DATA FROM A CONTINUOUS GLUCOSE MONITOR

(75) Inventors: Timothy Peter Engelhardt, Avon, IN (US); Nikolaus Schmitt, Heidelberg (DE); Phillip E. Pash, Indianapolis, IN (US); David Duke, Fishers, IN (US); Abhishek Soni, Indianapolis, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 302 days.

(21) Appl. No.: 12/975,769

(22) Filed: Dec. 22, 2010

(65) Prior Publication Data

US 2012/0166126 A1 Jun. 28, 2012

(51) Int. Cl.
| | | |
|---|---|---|
| G01C 19/00 | (2013.01) | |
| G01C 25/00 | (2006.01) | |
| G01D 18/00 | (2006.01) | |
| G01F 25/00 | (2006.01) | |
| G06F 19/00 | (2011.01) | |
| A61B 5/05 | (2006.01) | |
| A61B 5/00 | (2006.01) | |

(52) U.S. Cl.
USPC .......................... 702/104; 600/365; 600/347

(58) Field of Classification Search
USPC .................. 702/104; 600/365, 345, 347, 309
See application file for complete search history.

(56) References Cited

U.S. PATENT DOCUMENTS

| | | | |
|---|---|---|---|
| 6,254,586 B1 | 7/2001 | Mann et al. | |
| 6,424,847 B1 | 7/2002 | Mastrototaro et al. | |
| 6,895,263 B2 | 5/2005 | Shin et al. | |
| 6,931,327 B2 | 8/2005 | Goode, Jr. et al. | |
| 7,003,341 B2 | 2/2006 | Say et al. | |
| 7,029,444 B2 | 4/2006 | Shin et al. | |
| 7,190,988 B2 | 3/2007 | Say et al. | |
| 7,276,029 B2 | 10/2007 | Goode, Jr. et al. | |
| 7,599,726 B2 | 10/2009 | Goode, Jr. et al. | |
| 7,797,028 B2 | 9/2010 | Goode, Jr. et al. | |
| 7,801,591 B1 | 9/2010 | Shusterman | |
| 7,890,295 B2 | 2/2011 | Shin et al. | |
| 2005/0027180 A1 | 2/2005 | Goode, Jr. et al. | |
| 2007/0179367 A1 | 8/2007 | Ruchti et al. | |
| 2008/0119708 A1 | 5/2008 | Budiman | |
| 2009/0192751 A1* | 7/2009 | Kamath et al. ................ | 702/104 |
| 2010/0094111 A1* | 4/2010 | Heller et al. .................. | 600/345 |
| 2010/0179408 A1* | 7/2010 | Kamath et al. ................ | 600/365 |
| 2010/0298682 A1 | 11/2010 | Say et al. | |
| 2011/0021898 A1 | 1/2011 | Wei et al. | |

FOREIGN PATENT DOCUMENTS

WO 2009/146445 12/2009

*Primary Examiner* — Alexander H Taningco
*Assistant Examiner* — Manuel Rivera Vargas
(74) *Attorney, Agent, or Firm* — Harness, Dickey

* cited by examiner

(57) ABSTRACT

A method for calibrating a handheld diabetes managing device based on data generated by a continuous glucose monitor. The method can include sampling a current of the continuous glucose monitor at a sampling interval over a time period to generate a plurality of current samples for the time period. The method can also include determining a mean, median and standard deviation of the plurality of current samples. The blood glucose level of the patient can be measured at a first time and a calibration equation that associates the plurality of current samples with the estimated glucose level of the patient based on the measured blood glucose level and the plurality of current samples can be determined when the standard deviation is less than a first threshold and an absolute value of a difference between the mean and median is less than a second threshold.

25 Claims, 6 Drawing Sheets

CALIBRATION OF A HANDHELD DIABETES MANAGING DEVICE THAT RECEIVES DATA FROM A CONTINUOUS GLUCOSE MONITOR

FIELD

The present disclosure relates generally to medical devices and more particularly to a process for calibrating a blood glucose meter to estimate a patient's glucose level based on data received from a continuous glucose monitor and a self measured blood glucose measurement obtained from a blood glucose meter.

BACKGROUND

Medical devices are often used as diagnostic devices and/or therapeutic devices in diagnosing and/or treating medical conditions of patients. For example, a blood glucose meter is used as a diagnostic device to measure blood glucose levels of patients suffering from diabetes. An insulin infusion pump is used as a therapeutic device to administer insulin to patients suffering from diabetes.

Diabetes mellitus, often referred to as diabetes, is a chronic condition in which a person has elevated glucose levels that result from defects in the body's ability to produce and/or use insulin. There are three main types of diabetes. Type 1 diabetes can be autoimmune, genetic, and/or environmental and usually strikes children and young adults. Type 2 diabetes accounts for 90-95% of diabetes cases and is linked to obesity and physical inactivity. Gestational diabetes is a form of glucose intolerance diagnosed during pregnancy and usually resolves spontaneously after delivery.

In 2009, according to the World Health Organization, at least 220 million people worldwide suffer from diabetes. In 2005, an estimated 1.1 million people died from diabetes. The incidence of diabetes is increasing rapidly, and it is estimated that between 2005 and 2030, the number of deaths from diabetes will double. In the United States, nearly 24 million Americans have diabetes, and an estimated 25% of seniors age 60 and older are affected. The Centers for Disease Control and Prevention forecast that 1 in 3 Americans born after 2000 will develop diabetes during their lifetime. The National Diabetes Information Clearinghouse estimates that diabetes costs $132 billion in the United States alone every year. Without treatment, diabetes can lead to severe complications such as heart disease, stroke, blindness, kidney failure, amputations, and death related to pneumonia and flu.

Diabetes is managed primarily by controlling the level of glucose in the bloodstream. This level is dynamic and complex, and is affected by multiple factors including the amount and type of food consumed, and the amount of insulin (which mediates transport of glucose across cell membranes) in the blood. Glucose levels are also sensitive to exercise, sleep, stress, smoking, travel, illness, menses, and other psychological and lifestyle factors unique to individual patients. The dynamic nature of blood glucose and insulin, and all other factors affecting blood glucose, often require a person with diabetes to forecast blood glucose levels. Therefore, therapy in the form of insulin or oral medications, or both, can be timed to maintain blood glucose levels in an appropriate range.

Management of diabetes is time-consuming for patients because of the need to consistently obtain reliable diagnostic information, follow prescribed therapy, and manage lifestyle on a daily basis. Diagnostic information, such as blood glucose, is typically obtained from a capillary blood sample with a lancing device and is then measured with a handheld blood glucose meter. Interstitial glucose levels may be obtained from a continuous glucose sensor worn on the body. Prescribed therapies may include insulin, oral medications, or both. Insulin can be delivered with a syringe, an ambulatory infusion pump, or a combination of both. With insulin therapy, determining the amount of insulin to be injected can require forecasting meal composition of fat, carbohydrates and proteins along with effects of exercise or other physiologic states. The management of lifestyle factors such as body weight, diet, and exercise can significantly influence the type and effectiveness of a therapy.

Management of diabetes involves large amounts of diagnostic data and prescriptive data acquired in a variety of ways: from medical devices, from personal healthcare devices, from patient-recorded logs, from laboratory tests, and from healthcare professional recommendations. Medical devices include patient-owned bG meters, continuous glucose monitors, ambulatory insulin infusion pumps, diabetes analysis software, and diabetes device configuration software. Each of these systems generates and/or manages large amounts of diagnostic and prescriptive data. Personal healthcare devices include weight scales, blood pressure cuffs, exercise machines, thermometers, and weight management software. Patient recorded logs include information relating to meals, exercise and lifestyle. Lab test results include HbA1C, cholesterol, triglycerides, and glucose tolerance. Healthcare professional recommendations include prescriptions, diets, test plans, and other information relating to the patient's treatment.

There is a need for a handheld device to aggregate, manipulate, manage, present, and communicate diagnostic data and prescriptive data from medical devices, personal healthcare devices, patient recorded information, biomarker information, and recorded information in an efficient manner. The handheld device can improve the care and health of a person with diabetes so that the person with diabetes can lead a full life and reduce the risk of complications from diabetes.

Additionally, to effectively manage the care and health of the patient, there is a need for the handheld device to communicate with and process information received from other medical devices and systems. A handheld device may receive patient information from a number of different sources, such as an insulin pump, a continuous glucose monitor, a computer program, user input, etc. In order to accurately utilize this information, the handheld device may need to calibrate the information received from these sources. For example, a handheld diabetes managing device may receive, from a continuous glucose monitor, raw data that is related to a glucose level of a patient. In order to make use of this raw data, the handheld diabetes managing device may need to be calibrated to correlate the received raw data with a measured blood glucose level of the patient. The accuracy of this calibration can affect the care and treatment of the patient. Accordingly, there is a need for a method of calibrating a handheld diabetes managing device to determine an accurate estimated glucose level of a patient from data received from a continuous glucose monitor.

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

According to the present disclosure, a method for calibrating a handheld diabetes managing device to determine an estimated glucose level of a patient from data generated by a continuous glucose monitor is presented. The method can include the step of sampling a current of the continuous glucose monitor at a sampling interval over a time period to generate a plurality of current samples for the time period. The current can be related to a glucose level of the patient. The method can also include determining a mean of the plurality of current samples, determining a median of the plurality of current samples and determining a standard deviation of the plurality of current samples. Further, the method includes measuring the blood glucose level of the patient at a first time. Finally, the method includes determining a calibration equation that associates the plurality of current samples with the estimated glucose level of the patient based on the measured blood glucose level and the plurality of current samples when the standard deviation is less than a first threshold and an absolute value of a difference between the mean and median is less than a second threshold.

According to the present disclosure, a method for calibrating a handheld diabetes managing device to determine an estimated glucose level of a patient from data generated by a continuous glucose monitor is presented. The method can include sampling a current of the continuous glucose monitor at a sampling interval over a time period to generate a plurality of current samples for the time period, where the current is related to a glucose level of the patient. The method can also include determining a mean of the plurality of current samples, determining a median of the plurality of current samples, determining a standard deviation of the plurality of current samples, determining a 25% quantile value of the plurality of current samples, determining a 75% quantile value of the plurality of current samples, and determining a trend measure of the plurality of current samples. The trend measure can correspond to a change in the current over the time period. The method can further include measuring the blood glucose level of the patient at a first time. Additionally, the method can include determining a linear calibration equation that associates the plurality of current samples with the estimated glucose level of the patient based on the measured blood glucose level and the plurality of current samples when (i) the standard deviation is less than a first threshold, (ii) an absolute value of a difference between the mean and median is less than a second threshold, (iii) the median minus the 25% quantile value is less than a third threshold, (iv) the 75% quantile value minus the median is less than a fourth threshold, and (v) an absolute value of the trend measure is less than a fifth threshold.

A diabetes management system that periodically determines an estimated glucose level of a patient can include a continuous glucose monitor and a handheld diabetes managing device. The continuous glucose monitor can be configured to: (i) sample a current related to a glucose level of the patient at a sampling interval over a time period to generate a plurality of current samples for the time period, (ii) determine a mean of the plurality of current samples, (iii) determine a median of the plurality of current samples, and (iv) determine a standard deviation of the plurality of current samples. The handheld diabetes managing device can be in communication with the continuous glucose monitor. Further, the handheld diabetes managing device can be configured to: (i) measure the blood glucose level of the patient at a first time, (ii) receive the mean, median and standard deviation of the plurality of current samples from the continuous glucose monitor, (iii) determine a calibration equation that associates the plurality of current samples with the estimated glucose level of the patient based on the measured blood glucose level and the plurality of current samples when the standard deviation is less than a first threshold and an absolute value of a difference between the mean and median is less than a second threshold, and (iv) determine the estimated glucose level of the patient based on the calibration equation and the current sampled by the continuous glucose monitor.

Further areas of applicability of the present disclosure will become apparent from the detailed description provided hereinafter. It should be understood that the detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein.

DETAILED DESCRIPTION

Figure 1:
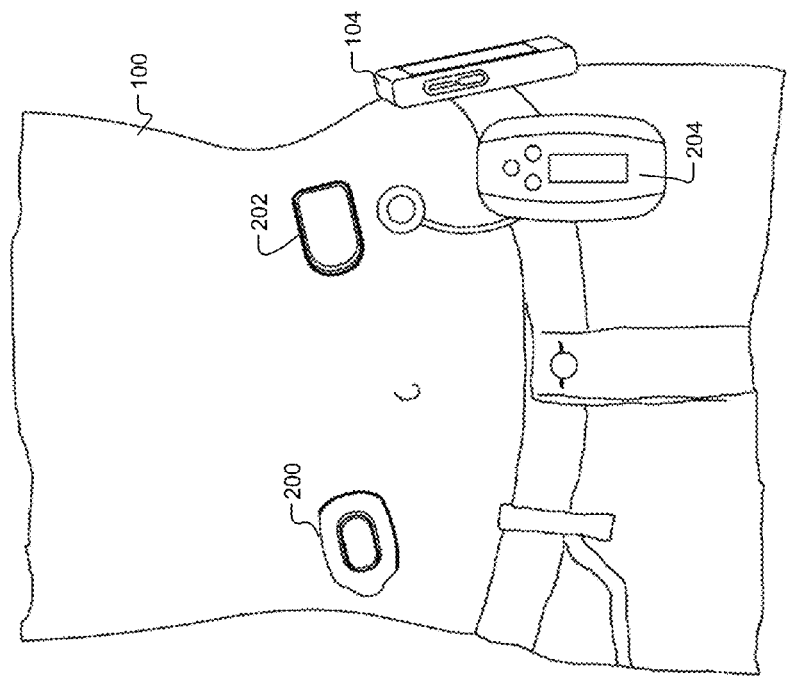
FIG. 1 shows a patient and a treating clinician.

Referring now to FIG. 1, a person 100 with diabetes and a healthcare professional 102 are shown in a clinical environment. Persons with diabetes include persons with metabolic syndrome, pre-diabetes, type 1 diabetics, type 2 diabetics, and gestational diabetics and are collectively referred to as a patient. Healthcare providers for diabetes are diverse and include nurses, nurse practitioners, physicians, and endocrinologists and are collectively referred to as a clinician.

During a healthcare consultation, the patient 100 typically shares with the clinician 102 a variety of patient data including blood glucose measurements, continuous glucose monitor data, amounts of insulin infused, amounts of food and beverages consumed, exercise schedules, and other lifestyle information. The clinician 102 can obtain additional patient data that includes measurements of HbA1C, cholesterol levels, triglycerides, blood pressure, and weight of the patient 100. The patient data can be recorded manually or electronically on a handheld diabetes managing device 104, a diabetes analysis software executed on a personal computer (PC) 106, and/or a web-based diabetes analysis site (not shown). The clinician 102 can analyze the patient data manually or electronically using the diabetes analysis software and/or the web-based diabetes analysis site. After analyzing the patient data and reviewing adherence of the patient 100 to previously prescribed therapy, the clinician 102 can decide whether to modify the therapy for the patient 100.

Figure 2:
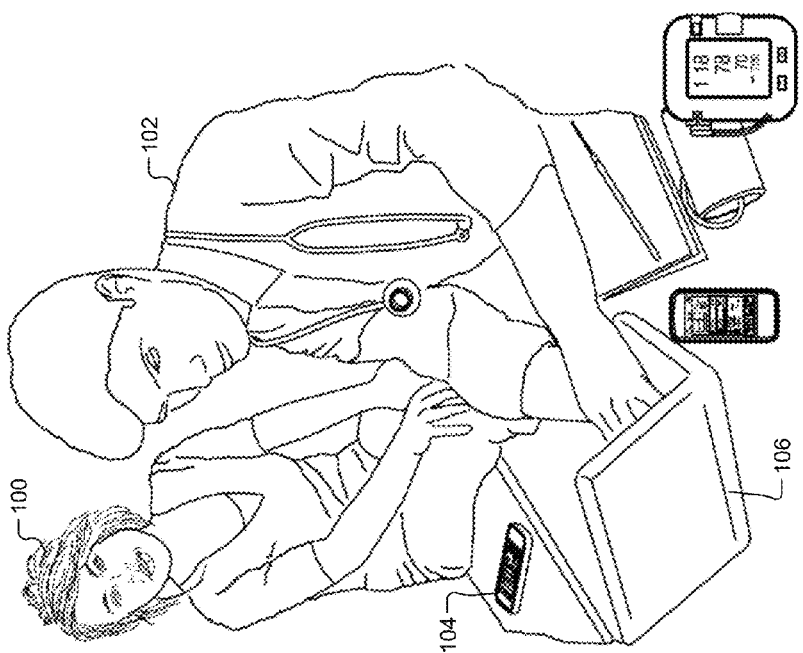
FIG. 2 shows a patient with a continuous glucose monitor (CGM), ambulatory durable insulin infusion pump, ambulatory non-durable insulin infusion pump, and diabetes manger.

Referring now to FIG. 2, the patient 100 can use a continuous glucose monitor (CGM) 200, an ambulatory durable insulin infusion pump 202 or an ambulatory non-durable insulin infusion pump 204 (collectively insulin pump 202 or 204), and the handheld diabetes managing device 104 (hereinafter the diabetes manager 104). The CGM 200 uses a subcutaneous sensor to sense and monitor the amount of glucose in the subcutaneous fluid of the patient 100 and communicates corresponding readings to the handheld diabetes managing device 104.

The diabetes manager 104 performs various tasks including measuring and recording blood glucose levels, determining an amount of insulin to be administered to the patient 100 via the insulin pump 202 or 204, receiving patient data via a user interface, archiving the patient data, etc. The diabetes manager 104 periodically receives readings from the CGM 200 indicating a glucose level in the subcutaneous fluid of the patient 100. The diabetes manager 104 transmits instructions to the insulin pump 202 or 204, which delivers insulin to the patient 100. Insulin can be delivered in the form of a bolus dose, which raises the amount of insulin in the blood of the patient 100 by a predetermined amount. Additionally, insulin can be delivered in a scheduled manner in the form of a basal dose, which maintains a predetermined insulin level in the blood of the patient 100.

Figure 3:
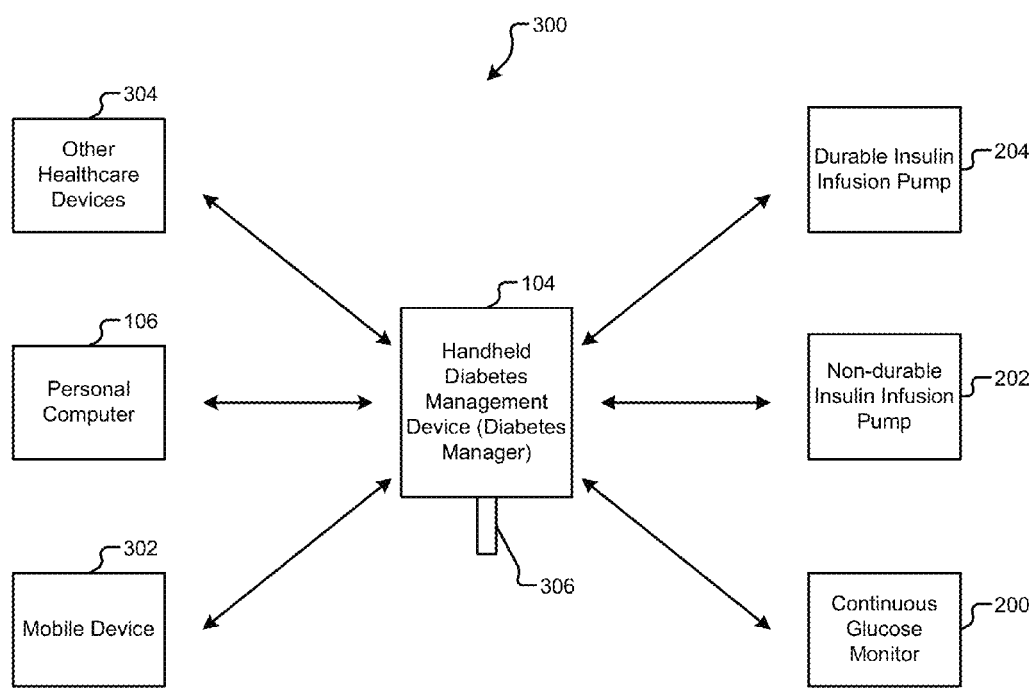
FIG. 3 shows a diabetes care system of systems used by patients and clinicians to manage diabetes.

Referring now to FIG. 3, a diabetes management system 300 used by the patient 100 and the clinician 102 includes one or more of the following devices: the diabetes manager 104, the continuous glucose monitor (CGM) 200, the insulin pump 202 or 204, a mobile device 302, the diabetes analysis software on the PC 106, and other healthcare devices 304. The diabetes manager 104 is configured as a system hub and communicates with the devices of the diabetes management system 300. Alternatively, the insulin pump 204 or the mobile device 302 can serve as the system hub. Communication between the various devices in the diabetes management system 300 can be performed using wireless interfaces (e.g., Bluetooth) and/or wireline interfaces (e.g., USB). Communication protocols used by these devices can include protocols compliant with the IEEE 11073 standard as extended using guidelines provided by Continua® Health Alliance Design Guidelines. Further, healthcare records systems such as Microsoft® HealthVault™ and Google™ Health can be used by the patient 100 and clinician 102 to exchange information.

The diabetes manager 104 can receive glucose readings from one or more sources (e.g., from the CGM 200). The CGM 200 continuously measures the glucose level of the patient 100. The CGM 200 periodically communicates the glucose level to the diabetes manager 104. The diabetes manager 104 and the CGM 200 communicate wirelessly using a proprietary Gazell wireless protocol developed by Nordic Semiconductor, Inc.

Additionally, the diabetes manager 104 includes a blood glucose meter (BGM) and a port that communicates with the BGM (both not shown). The port can receive a blood glucose measurement strip 306. The patient 100 deposits a sample of blood or other bodily fluid on the blood glucose measurement strip 306. The BGM analyzes the sample and measures the blood glucose level in the sample. The blood glucose level measured from the sample and/or the blood glucose level read by the CGM 200 can be used to determine the amount of insulin to be administered to the patient 100.

The diabetes manager 104 communicates with the insulin pump 202 or 204. The insulin pump 202 or 204 can be configured to receive instructions from the diabetes manager 104 to deliver a predetermined amount of insulin to the patient 100. Additionally, the insulin pump 202 or 204 can receive other information including meal and/or exercise schedules of the patient 100. The insulin pump 202 or 204 can determine the amount of insulin to administer based on the additional information.

The insulin pump 202 or 204 can also communicate data to the diabetes manager 104. The data can include amounts of insulin delivered to the patient 100, corresponding times of delivery, and pump status. The diabetes manager 104 and the insulin pump 202 or 204 can communicate using a wireless communication protocol such as Bluetooth. Other wireless or wireline communication protocols can also be used.

In addition, the diabetes manager 104 can communicate with other healthcare devices 304. For example, the other healthcare devices 304 can include a blood pressure meter, a weight scale, a pedometer, a fingertip pulse oximeter, a thermometer, etc. The other healthcare devices 304 obtain and communicate personal health information of the patient 100 to the diabetes manager 104 through wireless, USB, or other interfaces. The other healthcare devices 304 use communication protocols compliant with ISO/IEEE 11073 extended using guidelines from Continual® Health Alliance. The diabetes manager 104 can communicate with the other healthcare devices 304 using interfaces including Bluetooth, USB, etc. Further, the devices of the diabetes management system 300 can communicate with each other via the diabetes manager 104.

The diabetes manager 104 can communicate with the PC 106 using Bluetooth, USB, or other interfaces. A diabetes management software running on the PC 106 includes an analyzer-configurator that stores configuration information of the devices of the diabetes management system 300. The configurator has a database to store configuration information of the diabetes manager 104 and the other devices. The configurator can communicate with users through standard web or computer screens in non-web applications. The configurator transmits user-approved configurations to the devices of the diabetes management system 300. The analyzer retrieves data from the diabetes manager 104, stores the data in a database, and outputs analysis results through standard web pages or computer screens in non-web based applications.

The diabetes manager 104 can communicate with the mobile device 302 using Bluetooth. The mobile device 302 can include a cellular phone, a PDA, or a pager. The diabetes manager 104 can send messages to an external network through the mobile device 302. The mobile device 302 can transmit messages to the external network based on requests received from the diabetes manager 104.

In some embodiments, the CGM 200 measures the level of glucose in the interstitial fluid of the patient 100 by sampling a current. The level of glucose in the interstitial fluid, and therefore the sampled current, is related to the glucose level of the patient 100. In order to accurately estimate the glucose level of the patient 100 based on the interstitial fluid glucose level measured by the CGM 200, the diabetes manager 104 can be periodically calibrated.

The diabetes manager 104 can be calibrated by determining a calibration equation based on at least one current sample and at least one blood glucose measurement. The current sampled by the CGM 200 and the blood glucose level of the patient 100 can be assumed to have a linear relationship within a normal measurement region of approximately 40 to 400 Milligrams per Deciliter. Based on this assumed linear relationship, the calibration equation can be a linear equation that associates one or more current samples with an estimated glucose level of the patient. After calibration, the diabetes manager 104 can determine an estimated glucose level of the patient 100 based on the calibration equation and the current sampled by the CGM 200.

Figure 4:
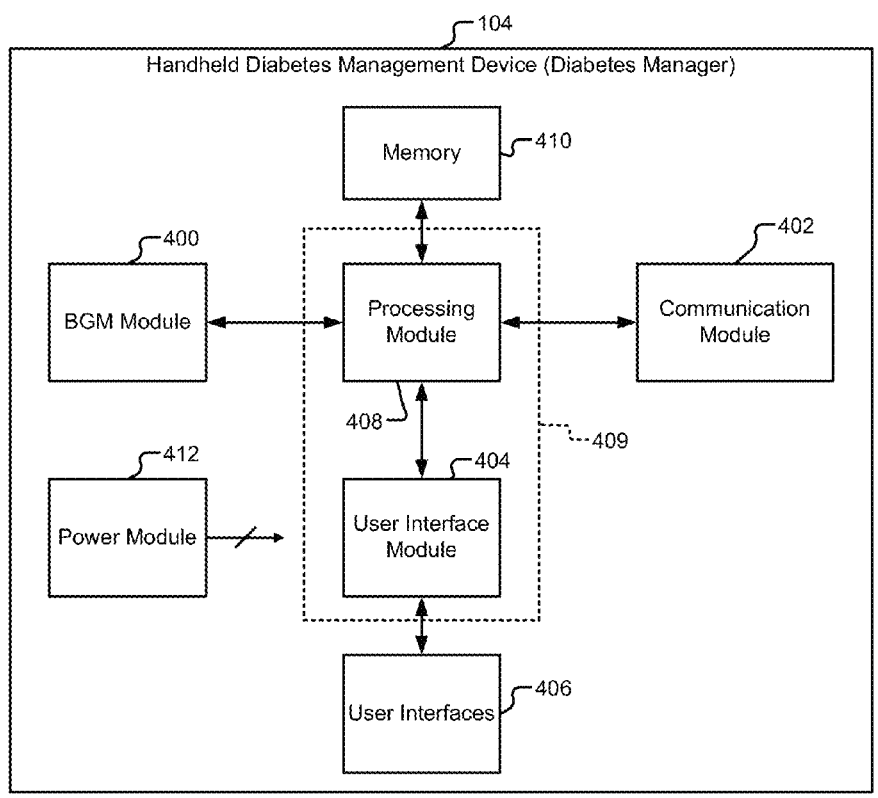
FIG. 4 is a functional block diagram of a diabetes manager.

Referring now to FIG. 4, an exemplary diabetes manager 104 includes a blood glucose measuring (BGM) module 400, a communication module 402, a user interface module 404, user interfaces 406, a processing module 408, memory 410, and a power module 412. The user interface module 404 and the processing module 408 can be implemented by an application processing module 409. The BGM module 400 includes a blood glucose measuring engine that analyzes samples provided by the patient 100 on the blood glucose measurement strip 306 and that measures the amount of blood glucose in the samples. The communication module 402 can include multiple radios that communicate with different devices of the diabetes management system 300. The user interface module 404 connects the diabetes manager 104 to various user interfaces 406 that the patient 100 can use to interact with the diabetes manager 104. For example, the user interfaces 406 can include keys, switches, a display, a speaker, a microphone, a secure digital (SD) card port, and/or a USB port (all not shown).

The processing module 408 processes data received from the BGM module 400, the communication module 402, and the user interface module 404. The processing module 408 uses memory 410 for processing and storing data. The memory 410 can include volatile and nonvolatile memory. The processing module 408 outputs data to and receives data from the user interfaces 406 via the user interface module 404. The processing module 408 outputs data to and receives data from the devices of the diabetes management system 300 via the communication module 402. The power module 412 supplies power to the components of the diabetes manager 104. The power module 412 can include a rechargeable battery or other source of power. The battery can be recharged, e.g., by using an adapter that plugs into a wall outlet and/or via a USB port on the diabetes manager 104.

Figure 5:
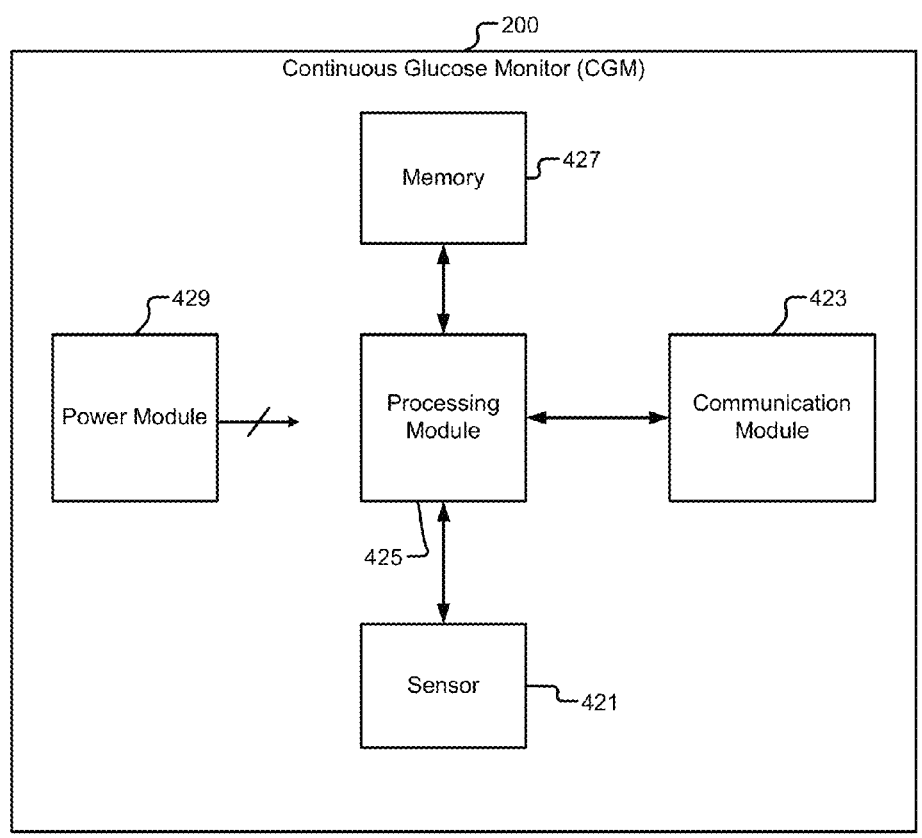
FIG. 5 is a functional block diagram of a continuous glucose monitor.

Referring now to FIG. 5, an exemplary continuous glucose monitor (CGM) 200 includes a sensor 421, a communication module 423, a processing module 425, memory 427, and a power module 429. The sensor 421 can monitor a condition of the patient 100 that is related to the glucose level of the patient 100. For example, the sensor 421, alone or in combination with processing module 425, can periodically sample a current value that corresponds to the level of glucose in the interstitial fluid of the patient 100. The communication module 423 can include one or more radios that communicate with different devices of the diabetes management system 300.

The processing module 425 processes data received from the sensor 421 and the communication module 423. The processing module 425 uses memory 427 for processing and storing data. The memory 427 can include volatile and nonvolatile memory. The processing module 425 outputs data to and receives data from the devices (for example, diabetes manager 104) of the diabetes management system 300 via the communication module 423. The power module 429 supplies power to the components of the CGM 200. In some embodiments, the power module 429 includes a battery or other source of power. The source of power may include a battery that can be recharged, e.g., by using an adapter that plugs into a wall outlet.

Figure 6:
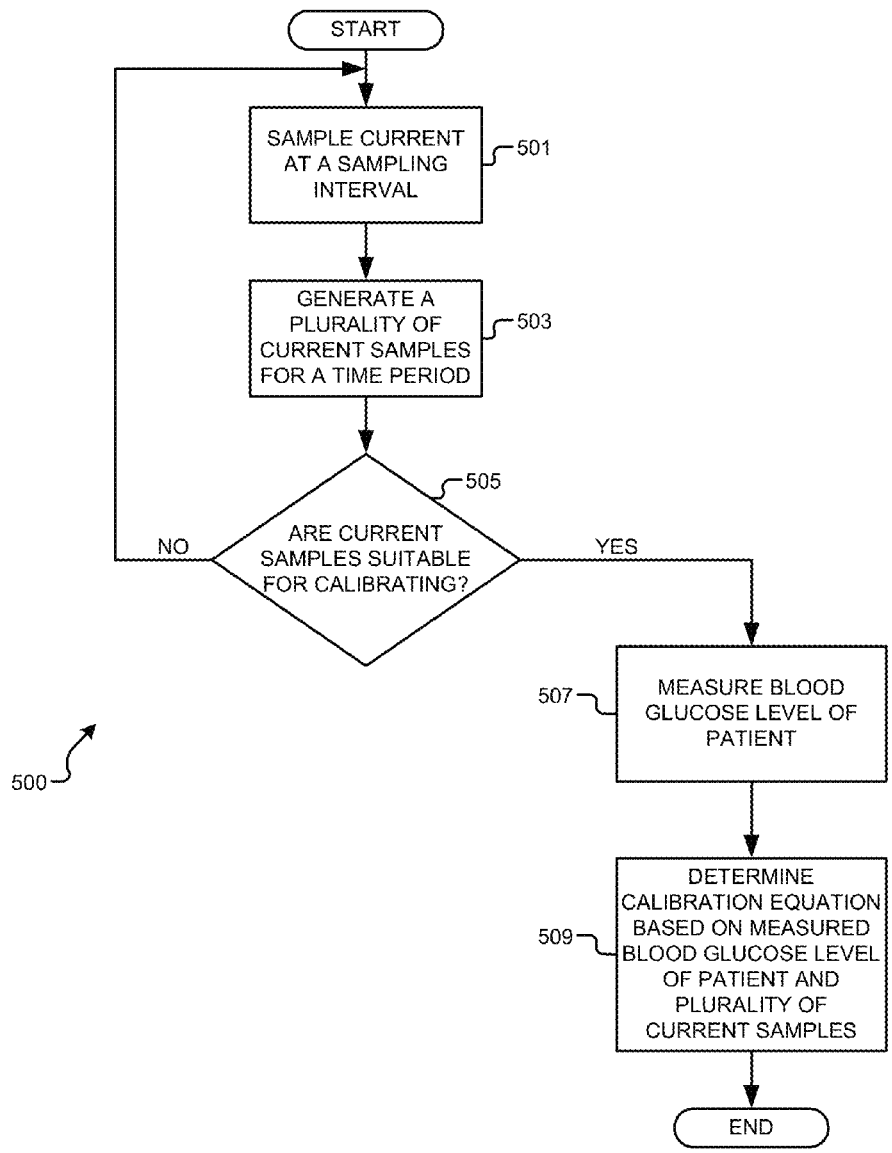
FIG. 6 shows a flow-chart illustrating an exemplary method of calibrating a handheld diabetes managing device according to the present disclosure.

Referring now to FIG. 6, an exemplary method 500 of calibrating a handheld diabetes managing device 104 to determine an estimated glucose level of a patient 100 from data generated by a continuous glucose monitor (CGM) 200 according to the present disclosure illustrated. The method 500 begins at step 501 where CGM 200 samples a current related to the glucose level of the patient 100 at a sampling interval. As described above, the current can be a measurement of the glucose level of the interstitial fluid of the patient 100, which in turn is related to the glucose level of the patient. For example only, the sampling interval can be one second, i.e., the CGM 200 can measure the current once per second.

At step 503, the CGM 200 can generate a plurality of current samples for a time period. In one example, if the sampling interval is one second and the time period is one minute, the CGM 200 will generate sixty current samples per time period.

In order to reduce the amount of information stored by the CGM 200 and/or transmitted to the diabetes manager 104, a plurality of current samples can be preprocessed. The CGM 200 may preprocess the plurality of current samples for the time period by determining one or more statistical values from the plurality of current samples. The statistical values can be representative of the plurality of current samples. Examples of statistical values include, but are not limited to, the mean, the median, the standard deviation, the 25% quantile and the 75% quantile of the plurality of current samples. Further statistical values can also be utilized by the calibration method 400, such as a trend measure that corresponds to the change in the current samples over the time period. The trend measure, discussed more fully below, can be utilized to indicate a direction and rate of change in the plurality of current samples. In this manner, the CGM 200 and/or diabetes manager 104 can store the statistical value(s) that are representative of the plurality of current samples for a time period, which can reduce the amount of data to be stored and transmitted. Furthermore, the statistical value(s) can be utilized by the CGM 200 and/or diabetes manager 104 for calibration purposes.

The plurality of current samples may contain erroneous or faulty measurements. For example, the current measured by the CGM 200 may contain sensor "noise" that causes a measured current sample to deviate from the actual glucose level of the patient 100. Such "noise" can be caused by, inter alia, physical movement of the CGM 200 relative to the patient 100 and/or electrical noise inherent within the CGM 200. Further, the CGM 200 may malfunction from time to time such that one or more current samples is substantially different from the actual glucose level of a patient 100, e.g., due to an internal issue in the electronics of the CGM 200 or sensor "dropout." Sensor "dropout" can occur due to physiological problems with the attachment of the CGM 200 to the patient 100, e.g., physical movement of the CGM 200 relative to the patient 100, such that one or more current samples "drop" to near zero even when the actual glucose level of the patient 100 is higher.

The method proceeds to step 505 at which the diabetes manager 104, alone or in combination with the CGM 200, determines whether the plurality of current samples is suitable for calibrating the diabetes manager 104. In some embodiments, the suitability for calibration of a plurality of current samples can be determined by the absence of sensor "noise" and/or "dropout" from the current samples. Sensor "noise" and/or "dropout" can be detected in many ways. For example only, a high rate of variability in the current samples over a time period can be indicative of sensor "noise" and/or "dropout." Therefore, different methods of determining a high rate of variability in the current samples can be utilized to determine the suitability of the current samples for calibration, as described below.

One method of determining whether the plurality of current samples is suitable for calibration is to compare the absolute value of the difference between the mean and median of the plurality of current samples with a threshold. In the event that the absolute value of the difference between the mean and median of the plurality of current samples is less than the threshold, the plurality of current samples can be deemed suitable for calibration. Similarly, in the event that the absolute value of the difference between the mean and median of the plurality of current samples is greater than the threshold, the plurality of current samples can be deemed unsuitable for calibration. This threshold can be set, for example, based on empirical data.

Another method of determining whether the plurality of current samples is suitable for calibration is to compare the standard deviation of the plurality of current samples with a threshold. In the event that the standard deviation of the plurality of current samples is less than the threshold, the plurality of current samples can be deemed suitable for calibration. Similarly, in the event that the standard deviation of the plurality of current samples is greater than the threshold, the plurality of current samples can be deemed unsuitable for calibration. This threshold can be set, for example, based on empirical data.

Yet another method of determining whether the plurality of current samples is suitable for calibration is to compare the median minus the 25% quantile value of the plurality of current samples with a threshold. In the event that the median minus the 25% quantile value of the plurality of current samples is less than the threshold, the plurality of current samples can be deemed suitable for calibration. Similarly, in the event that the median minus the 25% quantile value of the plurality of current samples is greater than the threshold, the plurality of current samples can be deemed unsuitable for calibration. This threshold can be set, for example, based on empirical data.

A further method of determining whether the plurality of current samples is suitable for calibration is to compare the 75% quantile value minus the median of the plurality of current samples with a threshold. In the event that the 75% quantile value minus the median of the plurality of current samples is less than the threshold, the plurality of current samples can be deemed suitable for calibration. Similarly, in the event that the 75% quantile value minus the median of the plurality of current samples is greater than the threshold, the plurality of current samples can be deemed unsuitable for calibration. This threshold can be set, for example, based on empirical data.

An additional method of determining whether the plurality of current samples is suitable for calibration is to compare the absolute value of a trend measure of the plurality of current samples with a threshold. The trend measure can correspond to the change in the current samples over the time period and can be a measure of a direction and rate of change in the plurality of current samples. A large trend measure may be indicative of a high rate of variability in a plurality of current samples. The trend measure can be determined by the following equation:

$$a_{Trend} := \frac{\sum_{i=1}^{N}(t_i - \bar{t})(y_i - \bar{y})}{\sum_{i=1}^{N}(t_i - \bar{t})^2}$$

wherein i=1, 2, . . . n where n is a number of samples in the time period; $y_i$ is the current at time i; $\bar{y}$ is the mean over the time period; $t_i$ is time at time i and the $\bar{t}$ is a mean of the time period. In the event that the absolute value of the trend measure of the plurality of current samples is less than the threshold, the plurality of current samples can be deemed suitable for calibration. Similarly, in the event that the absolute value of the trend measure of the plurality of current samples is greater than the threshold, the plurality of current samples can be deemed unsuitable for calibration. This threshold can be set, for example, based on empirical data.

While each of the methods discussed above has been described as independently determining whether a plurality of current samples is suitable for calibration, it should be appreciated that these methods can also be utilized in combination with each other. For example only, the suitability of a plurality of current samples for calibration can be determined by comparing the standard deviation of the plurality of current samples with a first threshold and by comparing the absolute value of the difference between the mean and median of the plurality of current samples with a second threshold. In the event that the standard deviation of the plurality of current samples is less than the first threshold and the absolute value of the difference between the mean and median of the plurality of current samples is less than a second threshold, the plurality of current samples can be deemed suitable for calibration. Similarly, in the event that the standard deviation of the plurality of current samples is greater than the threshold or the absolute value of the difference between the mean and median of the plurality of current samples is greater than the second threshold, the plurality of current samples can be deemed unsuitable for calibration.

If the plurality of current samples is not deemed suitable for calibration at step 505, the method 500 does not determine a calibration equation based on the plurality of current samples and returns to step 501. If, however, the plurality of current samples is determined to be suitable for calibration at step 505, the method 500 proceeds to step 507 at which the blood glucose level of the patient 100 is measured, e.g., by the diabetes manager 104. The diabetes manager 104 can provide an indication to the patient 100 that a blood glucose measurement is desired for calibration, e.g., by a visual, tactile and/or audible alarm. Typically, the patient 100 would then measure his or her blood glucose level by depositing a sample of blood or other bodily fluid on the blood glucose measurement strip 306 to be analyzed by the BGM module 400 associated with the diabetes manager 104, although other methods of blood glucose level measurement could be utilized.

After measuring the blood glucose level of the patient 100 at step 507, the diabetes manager 104 can determine a calibration equation based on the measured blood glucose level of the patient 100 and the plurality of current samples at step 509. In order to increase the accuracy of the calibration equation, the time at which the measurement of the blood glucose level of the patient 100 is taken (time of measurement) can correspond to the time period during which the plurality of current samples was sampled. It should be noted, however, that the time of measurement may not fall within the time period due to delay in the physiologic response of the patient 100, unsuitability of current samples for a time period, etc.

The calibration equation can be determined in a variety of ways. For example, if one assumes a linear relationship between the current sampled by the CGM 200 and the glucose level of the patient 100, the calibration equation can be a linear equation that is determined by applying a linear regression algorithm to the various data samples, i.e., the collection of measured blood glucose level/measured current pairs. The diabetes manager 104 can determine the calibration equation based on one measured blood glucose level/measured current associates pair by utilizing a predetermined reference pair (such as [0,0] for measured blood glucose level/measured current). Furthermore, as the diabetes manager 104/CGM 200 accumulates a number of calibration reference points (that is, measured blood glucose level/measured current pairs) these additional reference points can be utilized, in conjunction with or instead of the predetermined reference pair, to more accurately calibrate the diabetes manager 104. One skilled in the art will appreciate, however, that alternative techniques can be used by the diabetes manager 104 to determine the calibration equation.

Figure 7:
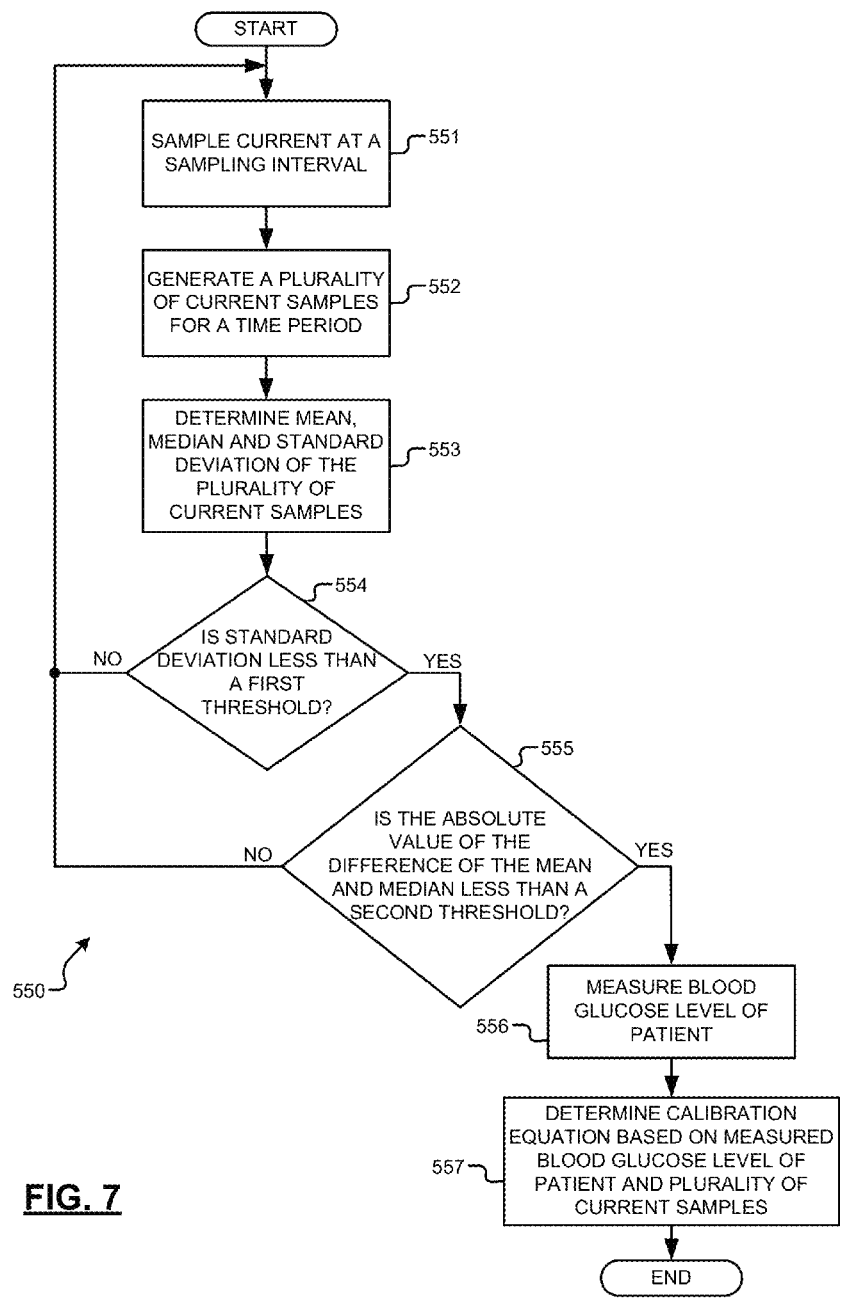
FIG. 7 shows a flow-chart illustrating another exemplary method of calibrating a handheld diabetes managing device according to the present disclosure.

Referring now to FIG. 7, another exemplary method 550 of calibrating a handheld diabetes managing device 104 to determine an estimated glucose level of a patient 100 from data generated by a continuous glucose monitor (CGM) 200 according to the present disclosure illustrated. Method 550 is similar to method 500 discussed above. The method 550 begins at step 551 where CGM 200 samples a current related to the glucose level of the patient 100 at a sampling interval. As described above, the current can be a measurement of the glucose level of the interstitial fluid of the patient 100, which in turn is related to the glucose level of the patient. For example only, the sampling interval can be one second, i.e., the CGM 200 can measure the current once per second. At step 552, the CGM 200 can generate a plurality of current samples for a time period. In one example, if the sampling interval is one second and the time period is one minute, the CGM 200 will generate sixty current samples per time period.

In order to reduce the amount of information stored by the CGM 200 and/or transmitted to the diabetes manager 104, a plurality of current samples can be preprocessed. The CGM 200 may preprocess the plurality of current samples for the time period by determining one or more statistical values from the plurality of current samples. The statistical values can be representative of the plurality of current samples and can be utilized to determine the suitability of the plurality of current samples for calibration, as discussed above. Accordingly, at step 553 the CGM 200 can determine the mean, median and standard deviation of the plurality of current samples. At step 554, the diabetes manager 104, alone or in combination with the CGM 200, determines whether the standard deviation of the plurality of current samples is below a first threshold. The first threshold can be set, for example, based on empirical data. If the standard deviation is greater than the first threshold at step 554, the method 500 does not determine a calibration equation based on the plurality of current samples and returns to step 551. If, however, the standard deviation is less than the first threshold, the method 500 proceeds to step 555.

The diabetes manager 104, alone or in combination with the CGM 200, determines whether the absolute value of the difference between the mean and median of the plurality of current samples is below a second threshold at step 555. The second threshold can be set, for example, based on empirical data. If the absolute value of the difference between the mean and median is greater than the second threshold at step 555, the method 500 does not determine a calibration equation based on the plurality of current samples and returns to step 551. If, however, the absolute value of the difference between the mean and median is less than the second threshold, the method 500 proceeds to step 556. In the exemplary method 550 shown in FIG. 7, the step of determining whether the plurality of current samples are suitable for calibrating (step 505 in FIG. 6) in method 500 has been replaced by steps 555 and 556, however, additional or alternative steps can be utilized, as discussed above.

At step 556, the blood glucose level of the patient 100 is measured, e.g., by the diabetes manager 104. The diabetes manager 104 can provide an indication to the patient 100 that a blood glucose measurement is desired for calibration, e.g., by a visual, tactile and/or audible alarm. Typically, the patient 100 would then measure his or her blood glucose level by depositing a sample of blood or other bodily fluid on the blood glucose measurement strip 306 to be analyzed by the BGM module 400 associated with the diabetes manager 104, although other methods of blood glucose level measurement could be utilized.

After measuring the blood glucose level of the patient 100 at step 556, the diabetes manager 104 can determine a calibration equation based on the measured blood glucose level of the patient 100 and the plurality of current samples at step 557. The calibration equation can be determined as described in regard to method 500 above.

The broad teachings of the disclosure can be implemented in a variety of forms. Therefore, while this disclosure includes particular examples, the true scope of the disclosure should not be so limited since other modifications will become apparent to the skilled practitioner upon a study of the drawings, the specification, and the following claims.

This detailed description is merely illustrative in nature and is in no way intended to limit the disclosure, its application, or uses. For purposes of clarity, the same reference numbers are used in the drawings to identify similar elements. As used herein, the phrase at least one of A, B, and C should be construed to mean a logical (A or B or C), using a non-exclusive logical or. It should be understood that steps within a method can be executed in different order without altering the principles of the present disclosure.

As used herein, the term module can refer to, be part of, or include an Application Specific Integrated Circuit (ASIC); an electronic circuit; a combinational logic circuit; a field programmable gate array (FPGA); a processor (shared, dedicated, or group) that executes code; other suitable components that provide the described functionality; or a combination of some or all of the above, such as in a system-on-chip. The term module can include memory (shared, dedicated, or group) that stores code executed by the processor.

The term code, as used above, can include software, firmware, and/or microcode, and can refer to programs, routines, functions, classes, and/or objects. The term shared, as used above, means that some or all code from multiple modules can be executed using a single (shared) processor. In addition, some or all code from multiple modules can be stored by a single (shared) memory. The term group, as used above, means that some or all code from a single module can be executed using a group of processors. In addition, some or all code from a single module can be stored using a group of memories.

The apparatuses and methods described herein can be implemented by one or more computer programs or applications executed by one or more processors. The computer programs and applications can include processor-executable instructions that are stored on a non-transitory tangible computer readable medium. The computer programs can also include stored data. Non-limiting examples of the non-transitory tangible computer readable medium are nonvolatile memory, magnetic storage, and optical storage.

What is claimed is:

1. A method for calibrating a handheld diabetes managing device to determine an estimated glucose level of a patient from data generated by a continuous glucose monitor, comprising:
   receiving, by a computer processor of a handheld diabetes managing device, a plurality of current samples sampled by a continuous glucose monitor over a time period, the current being related to a glucose level of the patient;
   determining, by the computer processor, a mean of the plurality of current samples;
   determining, by the computer processor, a median of the plurality of current samples;

determining, by the computer processor, a standard deviation of the plurality of current samples;

determining, by the computer processor, a quantile value of the plurality of current samples;

measuring a blood glucose level of the patient at a first time using the diabetes managing device, where the first time is proximate to the sampling time period and the diabetes managing device cooperatively operates with a test strip to measure the blood glucose level in a sample of blood residing on the test strip; and determining, by the computer processor, a calibration equation that associates the plurality of current samples with the estimated glucose level of the patient based on the measured blood glucose level and the plurality of current samples, wherein the determination of the calibration equation is in response to the standard deviation being less than a first threshold and an absolute value of a difference between the mean and the median being less than a second threshold and a difference between the median and the quantile being less than a third threshold.

2. The method of claim 1, further comprising determining a trend measure of the plurality of current samples, the trend measure corresponding to a change in the current over the time period, wherein the step of determining the calibration equation that associates the plurality of current samples with the estimated glucose level is performed in response to an absolute value of the trend measure being less than a fifth threshold.

3. The method of claim 2, wherein the step of determining the calibration equation that associates the plurality of current samples with the estimated glucose level is not performed in response to the absolute value of the trend measure being greater than the fifth threshold.

4. The method of claim 2, wherein the trend measure is determined by the equation:

$$a_{Trend} := \frac{\sum_{i=1}^{N}(t_i - \bar{t})(y_i - \bar{y})}{\sum_{i=1}^{N}(t_i - \bar{t})^2}$$

wherein i=1, 2, ... n where n is a number of samples in the time period; $y_i$ is the current at time i ; $\bar{y}$ is the mean over the time period; $t_i$ is time at time i and the $\bar{t}$ is a mean of the time period.

5. The method of claim 1, further comprising determining a 25% quantile value of the plurality of current samples, wherein the step of determining the calibration equation that associates the plurality of current samples with the estimated glucose level is performed in response to the median minus the 25% quantile value being less than a third threshold.

6. The method of claim 3, wherein the step of determining the calibration equation that associates the plurality of current samples with the estimated glucose level is not performed in response to the median minus the 25% quantile value being greater than a third threshold.

7. The method of claim 1, wherein the sampling interval is once per second.

8. The method of claim 7, wherein the time period is one minute.

9. The method of claim 1, further comprising determining a 75% quantile of the plurality of current samples, wherein the step of determining the calibration equation that associates the plurality of current samples with the estimated glucose level is performed in response to the 75% quantile value minus the median being less than a fourth threshold.

10. The method of claim 9, wherein the step of determining the calibration equation that associates the plurality of current samples with the estimated glucose level is not performed in response to the 75% quantile value minus the median being greater than the fourth threshold.

11. The method of claim 1, wherein the calibration equation includes a linear equation.

12. The method of claim 1, wherein the step of determining the calibration equation that associates the plurality of current samples with the estimated glucose level is not performed in response to the standard deviation being greater than the first threshold.

13. The method of claim 1, wherein the step of determining the calibration equation that associates the plurality of current samples with the estimated glucose level is not performed in response to the absolute value of the difference between the mean and median being greater than the second threshold.

14. The method of claim 1, further comprising determining, via the computer processor, the estimated glucose level of the patient based on the calibration equation and the current sampled by the continuous glucose monitor.

15. A device comprising:
a communication interface;
an input interface;
an output interface;
a memory capable of storing a first threshold and a second threshold; and
a processor coupled with the communication interface, the input interface and the memory, the processor being configured to
receive, via the communication interface, a plurality of current samples sampled at a sampling interval over a time period, the current being related to a glucose level of a patient,
determine a mean of the plurality of current samples,
determine a median of the plurality of current samples,
determine a standard deviation of the plurality of current samples,
determine a quantile of the plurality of current samples;
receive a value of a measured blood glucose level of the patient at a first time, the first time being proximate to the time period, the value being derived from a sample of a bodily fluid of the patient,
determine whether the standard deviation is less than a first threshold,
determine whether an absolute value of a difference between the mean and the median is less than a second threshold,
determine whether a difference between the median and the quantile is less than a third threshold and
in response to the standard deviation being less than the first threshold and the absolute value of the difference between the mean and the median being less than the second threshold and the difference between the median and the quantile being less than the third threshold, determine a calibration equation that associates the plurality of current samples with an estimated glucose level of the patient based on the plurality of current samples and the measured blood glucose level.

16. The device of claim 15, wherein the processor is further configured to provide an indicator, via the output interface, wherein the indicator indicates a request for the value of the measured blood glucose level of the patient.

17. The device of claim 16, wherein the indicator comprises at least one of a visual indicator, a tactile indicator, and an audible indicator.

18. The device of claim 15, wherein the processor is further configured to determine an estimated glucose level of the patient based on the calibration equation and the current sampled by the continuous glucose monitor; and present the estimated glucose level via the output interface.

19. The device of claim 15, wherein the communication interface comprises one or more of a wireless interface and a wireline interface.

20. A method for calibrating a handheld diabetes managing device to determine an estimated glucose level of a patient from data generated by a continuous glucose monitor, the method comprising:
receiving, by a computer processor of a handheld diabetes managing device, a plurality of current samples sampled by a continuous glucose monitor at a sampling interval over a time, the current being related to a glucose level of the patient;
determining, by the computer processor, a mean of the plurality of current samples;
determining, by the computer processor, a median of the plurality of current samples;
determining, by the computer processor, a standard deviation of the plurality of current samples;
determining, by the computer processor, a 25% quantile value of the plurality of current samples;
determining, by the computer processor, a 75% quantile value of the plurality of current samples;
determining, by the computer processor, a trend measure of the plurality of current samples, the trend measure corresponding to a change in the current over the time period;
measuring a blood glucose level of the patient at a first time using the diabetes managing device, where the first time is proximate to the sampling time period and the diabetes managing device cooperatively operates with a test strip to measure the blood glucose level in a sample of blood residing on the test strip; and
determining, by the computer processor, a linear calibration equation that associates the plurality of current samples with the estimated glucose level of the patient based on the measured blood glucose level and the plurality of current samples, wherein the determination of the calibration equation is in response to (i) the standard deviation being less than a first threshold, (ii) an absolute value of a difference between the mean and median being less than a second threshold, (iii) the median minus the 25% quantile value being less than a third threshold, (iv) the 75% quantile value minus the median being less than a fourth threshold, and (v) an absolute value of the trend measure being less than a fifth threshold.

21. The method of claim 20, wherein the step of determining the calibration equation that associates the plurality of current samples with the estimated glucose level is not performed in response to (i) the standard deviation being greater than the first threshold, (ii) an absolute value of a difference between the mean and median being greater than the second threshold, (iii) the median minus the 25% quantile value being greater than the third threshold, (iv) the 75% quantile value minus the median being greater than the fourth threshold, or (v) the absolute value of the trend measure being greater than the fifth threshold.

22. The method of claim 20, wherein the trend measure is determined by the equation:

$$a_{Trend} := \frac{\sum_{i=1}^{N} (t_i - \bar{t})(y_i - \bar{y})}{\sum_{i=1}^{N} (t_i - \bar{t})^2}$$

wherein i=1, 2, ... n where n is a number of samples in the time period; $y_i$ is the current at time i; $\bar{y}$ is the mean over the time period; $t_i$ is time at time i and the $\bar{t}$ is a mean of the time period.

23. The method of claim 20, further comprising determining, via the computer processor, the estimated glucose level of the patient based on the linear calibration equation and the current sampled by the continuous glucose monitor.

24. A diabetes management system that periodically determines an estimated glucose level of a patient, the diabetes management system comprising:
a continuous glucose monitor configured to: (i) sample a current related to a glucose level of the patient at a sampling interval over a time period to generate a plurality of current samples for the time period, and (ii) transmit the plurality of current samples; and
a handheld diabetes managing device in communication with the continuous glucose monitor and configured to: (i) receive, via a computer processor of the handheld diabetes managing device, the plurality of current samples from the continuous glucose monitor, (ii) determine, via the computer processor, a mean of the plurality of current samples, (iii) determine, via the computer processor, a median of the plurality of current samples, (iv) determine, via the computer processor, a standard deviation of the plurality of current samples, (v) measure a blood glucose level of the patient at a first time in cooperation with a test strip having a sample of blood residing thereon, the first time being proximate to the sampling time period, (vi) determine, via the computer processor, a calibration equation that associates the plurality of current samples with the estimated glucose level of the patient based on the measured blood glucose level and the plurality of current samples, wherein the handheld diabetes managing device determines the calibration equation in response to the standard deviation being less than a first threshold and an absolute value of a difference between the mean and median being less than a second threshold and a difference between the median and a quantile of the plurality of current samples being less than a third threshold, and (vii) determine, via the computer processor, the estimated glucose level of the patient based on the calibration equation and the current sampled by the continuous glucose monitor.

25. The diabetes management system of claim 24, wherein the handheld diabetes managing device is further configured to disregard the plurality of current samples in determining the calibration equation in response to the standard deviation being greater than the first threshold or the absolute value of the difference between the mean and median being greater than the second threshold.

* * * * *

UNITED STATES PATENT AND TRADEMARK OFFICE
CERTIFICATE OF CORRECTION

PATENT NO. : 8,589,106 B2  
APPLICATION NO. : 12/975769  
DATED : November 19, 2013  
INVENTOR(S) : Engelhardt et al.

It is certified that error appears in the above-identified patent and that said Letters Patent is hereby corrected as shown below:

In the Specification:

Column 5, line 30, before "204", insert --202 or--.

Column 9, line 60, delete "$y_i$is", insert --$y_i$ is--.

Column 9, line 61, delete "$t_i$is", insert --$t_i$ is--.

In the Claims:

Column 13, Claim 4, line 46, delete "i ;", insert --i;--.

Column 13, Claim 6, line 55, delete "claim 3", insert --claim 5--.

Column 14, Claim 15, line 33, after "to", insert --:--.

Column 14, Claim 15, line 53, delete "threshold and", insert --threshold, and--.

Signed and Sealed this  
Tenth Day of June, 2014

Michelle K. Lee  
*Deputy Director of the United States Patent and Trademark Office*